United States Patent [19]

Lo et al.

[11] Patent Number: 5,055,400

[45] Date of Patent: Oct. 8, 1991

[54] LEUKOTOXIN GENE OF PASTEURELLA HAEMOLYTICA

[75] Inventors: Reggie Y. C. Lo; Patricia E. Shewen, both of Guelph; Craig A. Strathdee, Mississauga, all of Canada

[73] Assignee: University of Guelph, Ontario, Canada

[21] Appl. No.: 935,493

[22] Filed: Nov. 26, 1986

[51] Int. Cl.[5] .................. C12P 21/02; C12P 19/34; C12N 15/00; C12N 1/21; C12N 7/00; C12N 15/12

[52] U.S. Cl. .................. 435/69.1; 435/91; 435/172.3; 435/320.1; 435/252.33; 435/235.1; 536/27

[58] Field of Search .............. 435/320, 68, 172.3, 435/252.33, 235, 91; 536/27

[56] References Cited

U.S. PATENT DOCUMENTS

| | | | |
|---|---|---|---|
| 4,446,237 | 5/1984 | Berninger | 436/504 |
| 4,556,643 | 12/1985 | Paau et al. | 436/501 |
| 4,957,739 | 9/1988 | Berget et al. | 424/92 |

OTHER PUBLICATIONS

Strathdu et al., (1987) Extensive Homology Between the Leukotoxin of *Pasteurella Hacmolytica* A1 and the alpha–Hemolysin of Eschenchia coli. Infer. and Immun. 55, 3233–3236.

Lo, et al. (1985) Cloning and Expression of the Leukotoxin Gene of *Pasteurella Haemohytica* A1 in *Eschenchia coli* KIL. Infec. & Immun. 50, 667–671.

Sanger et al., (1977) DNA Sequencing With Chain Termination Inhibitors Proc. Natl. Acad. Sci. U.S.A. 74, 5463–5467.

Messing J. (1983) New M13 Vector for Choning, Meth. Enzymol 101, 20–89.

Lo et al., (1987) Nucliptide Sequence of the Leukotoxin Gener of *Pasteurella Haemolytica* A1. Infec. and Immun. 55, 1987–1996.

Old et al., (eds.) 1985 in: *Principles of Grane Manipulation. An Introduction to Genetic Engineering.* Third Edition, Blackwell Sci. Publ. pp. 3–19, 102–152.

Shewen et al., 1983. Am. J. Vet. Res. 44, 715–719.

Schewan et al., 1985, Am. J. Vet. Res. 46, 1212–1214.

Baluyut et al., 1981, Am. J. Vet. Res. 42, 1920–1926.

Shewen et al., Abstract, North American Symposium on Bovine Respiratory Disease, Amarillo, Texas, (Sep., 1983), p. 480.

*Primary Examiner*—Elizabeth C. Weimar
*Assistant Examiner*—Christopher Low
*Attorney, Agent, or Firm*—Sughrue, Mion, Zinn Macpeak & Seas

[57] ABSTRACT

The gene coding for *Pasteurella haemolytica* leukotoxin can be cloned in a plasmic expressed in *Escherichia coli*. The leukotoxin gene can be isolated from a clone bank of *P. haemolytica*. The clone bank is constructed by partial digestion of genomic DNA. The resultant 5 to 10 kilobase-pair fragments are ligated into plasmid vector pBR322. The resultant clones are screened for the production of *P. haemolytica* soluble antigens by a colony enzyme-linked immunosorbent assay blot method with a rabbit antiserum raised against the soluble antigens. The clones producing *P. haemolytica* soluble antigens are then analyzed for the production of the leukotoxin by a cytotoxicity assay with cells from a bovine leukemia-derived B-lymphocyte cell line as the target cells. Positive clones are identified, and subsequent restriction analysis of the recombinant plasmids shows the same insert DNA is cloned in the plasmid vector. The DNA sequence analysis of the insert DNA reveals regions coding for the leukotoxin.

20 Claims, 3 Drawing Sheets

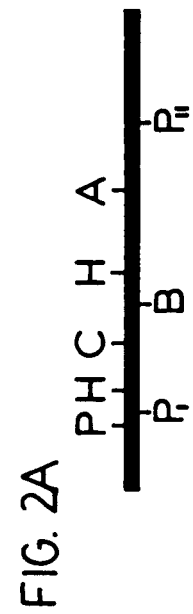
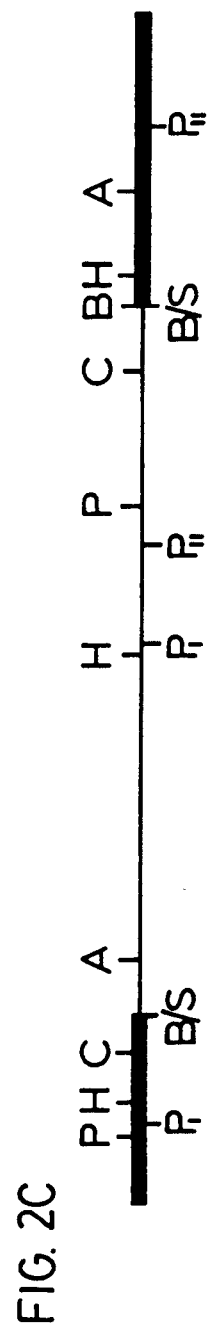
FIG. 2A
FIG. 2B
FIG. 2C

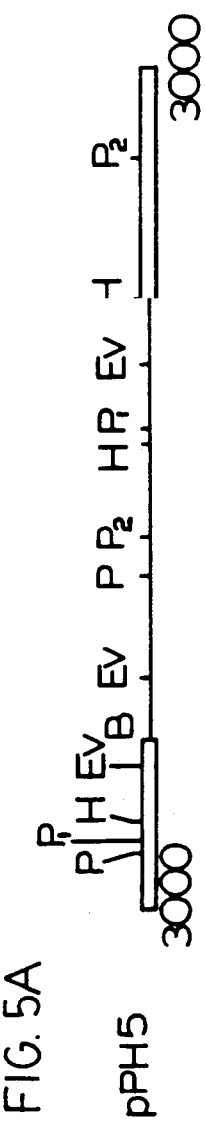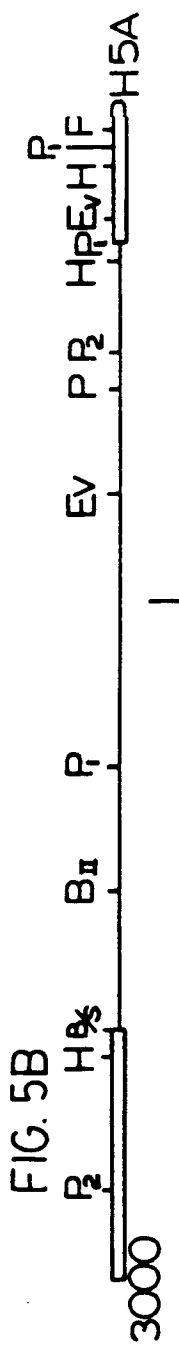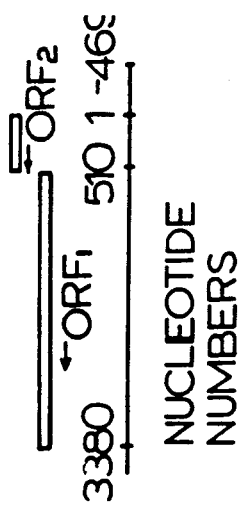

LEUKOTOXIN GENE OF PASTEURELLA HAEMOLYTICA

FIELD OF THE INVENTION

This invention relates to the cloning and expression of the leukotoxin gene of *Pasteurella haemolytica* in a suitable host microorganism.

BACKGROUND OF THE INVENTION

Bovine pneumonic pasteurellosis associated with *Pasteurella haemolytica* A1 is a major cause of sickness and death in feedlot cattle. Although vaccination with this organism might be expected to produce immunity to the disease, experimental trials and field studies using conventional formalinized bacterins have failed to show a protective effect, in fact, vaccinated animals are frequently more suspceptible to the disease than their non-vaccinated counterparts.

Immunization with live *P. haemolytica* has been shown to protect cattle against experimental challenge exposure to the bacterium. *P. haemolytica* produces a cytotoxin with specificity for ruminant leukocytes. This may contribute to the pathogenesis of pneumonic pasteurellosis by impairing primary lung defense and subsequent immune response or by induction of inflammation as a consequence of leukocyte lysis.

The protective capability of cytotoxic supernate from *P. haemolytica* has been used as a vaccine. This preparation contains numerous soluble antigens from the bacterium which may be important in protection. These soluble antigens include a ruminant-leukocyte-specific cytotoxin, serotype-specific soluble surface antigens, neuraminidase and protease. An example of such vaccine and its development is disclosed in applicant's copending U.S. patent application Ser. No. 821,197 filed Jan. 22, 1986. Developments of vaccines from the crude cytotoxic supernate requires the purification and characterization of these antigens which can become a difficult and costly process.

Recent advances in molecular biology have provided a new approach in the characterization of bacterial determinants involved in pathogenicity. The particular genes which code for bacterial antigens can be isolated by molecular cloning using various recombinant DNA techniques. For example, it is known the genes which code for the heat-labile enterotoxins of *E. coli* of porcine and human origin have been isolated. The cholera toxin genes from *Vibrio cholera* have also been isolated using the cloned *E. coli* elt genes as a hybridization probe. Genes encoding the enzymatic moiety of the exotoxin A from *Pseudomonas aeruginosa* and the phospholipase C determinant of *P. aeruginosa* have also been successfully cloned and expressed in *E. coli*. These cloned genes greatly facilitate the analyses of the pathogenic and immunogenic characteristics of the toxin protein products as well as enabling the characterization of the genetic organization and regulation of expression of these bacterial toxins. Hence, an alternative method involving the isolating of genes coding for the soluble antigens of *P. haemolytica* would be an important advance over existing vaccine developed from culture supernatant.

SUMMARY OF THE INVENTION

According to an aspect of the invention a nucleotide sequence coding for leukotoxin which is a protein produced by the metabolism of *Pasteurella haemolytica* is provided.

According to another aspect of the invention a recombinant plasmid may be developed which includes the nucleotide sequence coding for the leukotoxin.

According to another aspect of the invention a phage may be developed having the nucleotide sequence.

According to another aspect of the invention the nucleotide sequence is a DNA fragment of approximately 8.7 kbp.

According to another aspect of the invention a microorganism may be transformed with the recombinant plasmid and, in particular, may be that having the identifying characteristics of ATCC deposition #86/025.

According to another aspect of the invention, the nucleotide sequence of the leukotoxin may be altered to produce modified derivatives of the leukotoxin.

According to another aspect of the invention a process for producing a foreign proteinaceous leukotoxin having a molecular weight of approximately 100,000 daltons comprises transforming a micro-organism with the nucleotide sequence. The transformed micro-organism is then cultured under suitable conditions to yield the leukotoxin. Accordingly, the leukotoxin may be isolated and a vaccine may be developed against *Pasteurella haemolytica* by mixing isolated leukotoxin and/or its derivatives with suitable carriers.

According to another aspect of the invention polyclonal and monoclonal antibodies may be raised to the leukotoxin and/or derivatives.

According to another aspect of the invention the entire nucleotide sequence or a portion thereof may be used as a DNA probe.

BRIEF DESCRIPTION OF THE DRAWINGS

Preferred embodiments of the invention are exemplified in the drawings wherein:

FIGS. 2A, 2B, and 2C are restriction maps of the recombinant plasmids which contain the *Pasteurella haemolytica* leukotoxin gene;

FIGS. 5A, 5B, 5C, and 5D are restriction maps of additional recombinant plasmids which contain the *P. haemolytica* leukotoxin gene.

DETAILED DESCRIPTION OF THE PREFERRED EMBODIMENTS

Figure 1:
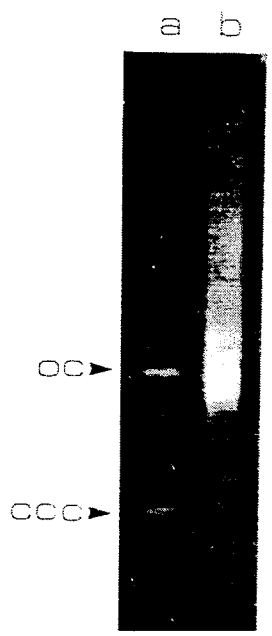
FIG. 1 is an Agarose gel electrophoresis profile of the *Pasteurella haemolytica* plasmid clone bank.

Based on the work disclosed in applicant's copending U.S. patent application Ser. No. 821,197, non-viable vaccines protecting calves against experimental challenge by intrabronchular inoculation with live *P. haemolytica* can be developed from the culture supernatant. Vaccinated calves had significantly lower pneumonic scores based on clinical signs and postmortem lesions compared to unvaccinated calves or bacterin vaccinated calves. As noted, however, such vaccines include other antigens aside from the leukotoxin present in the culture supernate. In an attempt to locate a DNA sequence which might code for the leukotoxin, as expressed in *P. haemolytica*, a clone bank of *P. haemolytica* A1 genomic DNA was constructed in *Escherichia coli* using the plasmid vector pBR322. From this clone bank, a collection of recombinant plasmids coding for the soluble antigens of *P. haemolytica* A1 were isolated. The *E. coli* clones were screened for the presence of *P. haemolytica* antigens by the colony ELISA technique (enzyme-linked immunosorbant assay) using a rabbit antiserum related to the soluble antigens of *P. haemolytica* A1. From this collection, plasmids coding for the leukotoxin were identified by screening protein preparations from the *E. coli* clones for leukotoxin activity using the neutral red assay. The presence of the leukotoxin in the *E. coli* cells was confirmed by serum neutralization using both rabbit and calf sera. The cloned leukotoxin was identified as a protein having a molecular weight of approximately 100,000 daltons. Such identification was through SDS-PAGE and Western blot analysis of the cytoplasmic proteins from the *E. coli* clones. DNA sequence analysis revealed the complete sequence of the leukotoxin gene on the cloned fragment in the plasmid.

Looking specifically at the methodology and techniques for isolating and identifying the leukotoxin gene, the following demonstrates a preferred embodiment thereof. In the following procedures and examples, the materials and methods were:

Bacteria and Plasmid Strains

*P. haemolytica* A1 ATCC 43270 (biotype A, serotype 1) was originally obtained from E. L. Biberstein, University of California, Davis. Stock organisms were maintained as lyophilized cultures after freeze-drying in distilled water containing (wt/vol) 5% dextran (molecular weight, 70,000), 7% sucrose, and 1% monosodium glutamate.

*Escherichia coli* HB101 used as the recipient, and plasmid pBR322 was used as the vector for the construction of the clone bank. The *E. coli* HB101 is characterized by deposit at ATCC 33694. Their genotypes and characteristics were described by Maniatis et al (1982, Molecular cloning: a laboratory manual; Cold Spring Harbor Laboratory, Cold Spring Harbor, N.Y.) and Bolivar et al (1977, Construction and characterization of new cloning vehicles. II. A multipurpose cloning system; Gene 2:95–113), respectively.

Media, Enzymes, and Chemicals

*P. haemolytica* was cultured in brain heart infusion broth (Difco Laboratories, Detroit, Mich.) while *E. coli* cultures were grown in LT medium as described by R. Y. C. Lo and L. A. Cameron, A Sample Immunological Detection Method for the Direct Screening of Genes from Clone Banks (Can. J. of Biochem. and Cell Biol., Vol 64, No 1, 73–76, 1986). Where appropriate the antibiotics ampicillin and tetracycline were supplemented at 100 and 12.5 mg/liter, respectively, after the medium was autoclaved. Restriction endonuclease, T4 DNA ligase, *E. coli* DNA polymerase I, and bacterial alkaline phosphate were purchased from Bethesda Research Laboratories, Inc., Gaithersburg, Md.; GIBCO, Burlington, Ontario, Canada; or Boehringer Mannheim, Dorval, Quebec, Canada and used as described by the suppliers. Low-melting-point agarose was from Bethesda Research Laboratories. [alpha-$^{32}$P]dATP (3,000 Ci/mmol) was purchased from New England Nuclear Corp., Lachine, Quebec.

PROCEDURE 1

Construction of a Clone Bank of *P. haemolytica* DNA in *E. coli*

A clone bank of *P. haemolytica* A1 was constructed by the method of Nasmyth and Reed (1980, Isolation of genes by complementation in yeast: molecular cloning of a cell-cycle gene. Proc. Natl. Acad. Sci. USA 77:2119–2123). Genomic DNA was extracted from *P. haemolytica* A1 by sodium dodecyl sulfate (SDS) lysis of the bacterial cells and phenol extraction (Marmer, J. 1961. A procedure for the isolation of deoxyribonucleic acid from microorganisms. J. Mol. Biol. 3:208–218). The DNA was then partially digested by the restriction endonuclease Sau3A, and fragments of 5 to 10 Kilobase pairs were recovered by a sucrose gradient centrifugation by the method of Maniatis et al (1978. The isolation of structural genes from libraries of eukaryotic DNA, Cell 15: 687–701). These fragments were inserted into the unique BamHI site of the plasmid vector pBR322 which had been dephosphorylated by bacterial alkaline phosphatase. The ligated DNA mixture was transformed into *E. coli* competent cells, and recombinants were recovered by selecting for ampicillin-resistant (Amp$^r$) colonies. The recombinants were pooled and amplified in broth cultures, and plasmid DNA was prepared by cesium chloride-ethidium bromide centrifugation (Thompson, R., S. G. Hughes, and P. Broda. 1974. Plasmid identification using specific endonucleases. Mol. Gen. Genet. 133:141–149) and stored at −20° C.

PROCEDURE 2

Preparation of Rabbit Antiserum to Soluble Antigens and Screening of the Clone Bank New Zealand White rabbits (Riemens Fur Ranches Ltd., St. Agatha, Ontario, Canada) were immunized with lyophilized *P. haemolytica* culture supernatant prepared essentially as described previously (Shewen, P. E., and B. N. Wilkie. 1982. Cytotoxin of *Pasteurella haemolytica* acting on bovine leukocytes. Infec. Immun. 35:91–94) except that 7% autologous rabbit serum was substituted for fetal bovine serum in the growth medium. Each rabbit received a total of seven inoculations of 10 mg of crude superantant in 1 ml of saline, divided equally intradermally and intravenously, at intervals of 10 to 12 days. The first two intradermal inoculations were emulsified in complete Freund adjuvant (Difco). Serum was collected 1 week after the seventh immunization. This serum had a titer to *P. haemolytica* surface antigens of 1/32, as measured by direct bacterial agglutination (Shewen, P. E., and B. N. Wilkie. 1982. Antibody titer to *Pasteurella haemolytica* A1 in Ontario beef cattle. Can. J. Comp. Med. 46:354–356), and a neutralizing titer to *P. haemolytica* leukotoxin of 1/640, as measured in the micro-plate assay described below.

The antibody preparation was used to screen the clone bank for production of *P. haemolytica* antigens by the colony enzyme-linked immunosorbent assay (ELISA) blot method (Lo and Cameron, supra). Briefly, the *E. coli* recombinant clones were grown on nitrocellulose paper, and the cells were lysed with chloroform vapor. The nitrocellulose paper was immersed in a blocking solution of TBS buffer (20 mM Tris hydrochloride [pH 7.5], 500 mM NaCl) containing 3% gelatin, 150 mM NaCl, 5 mM $MgCl_2$, 1 ug of DNase I per ml, and 40 ug of lysozyme per ml for 1 h and then inoculated with the rabbit antiserum (1/200 dilution) in TBS buffer overnight. After being washed twice in TBS buffer, the nitrocellulose paper was reacted with goat anti-rabbit immunoglobulin G (IgG) conjugated with horseradish peroxidase (Bio-Rad Laboratories, Mississauga, Ontario, Canada) at a 1/2,000 dilution in TBS buffer for 1 h. The blots were washed twice in TBS buffer and developed in horseradish peroxidase color development reagents (Bio-Rad).

PROCEDURE 3

Agarose Gel Electrophoresis and Southern Blot Analysis

The restriction fragments of the recombinant plasmids were analyzed by agarose gel electrophoresis as previously described by Lo and Cameron, (supra). For Southern blot analysis (Southern, E. M. 1975. Detection of specific sequences among DNA fragments separated by gel electrophoresis. J. Mol. Biol. 98:503–517), *P. haemolytica* genomic DNA was digested with an appropriate restriction endonuclease, electrophoresed on an agarose gel, and blotted onto nitrocellulose paper by electrophoretic transfer. The DNA fragments to be used as probes were recovered from the recombinant plasmids after enzyme digestion and purification on low-melting-point agarose gels by the method of Wieslander (Weislander, L. 1979. A simple method to recover intact high molecular weight RNA and DNA after electrophoretic separation in low gelling temperature agarose gels. Anal. Biochem. 98:305–309) and labeled with [alpha-$^{32}$P]dATP by nick-translation by the procedure of Rigby et al (Rigby, P. W. J., M. Dieckmann, C. Rhodes, and P. Berg. 1977. Labelling deoxyribonucleic acid to high specific activity in vitro by nick translation with DNA polymerase I.J. Mol. Biol. 113:237–251).

PROCEDURE 4

Preparation of Periplasmic and Cellular Proteins

The *E. coli* cells carrying the recombinant plasmids were subjected to osmotic shock treatment by the method of Neu and Heppel (1965. The release of enzymes from *Escherichia coli* by osmotic shock and during the formation of spheroplasts. J. Biol. Chem. 240:3685–3692). The resulting cell suspension was stirred for 10 min on ice and then centrifuged, and the supernatant was recovered. The supernatant was adjusted to 0.01M Tris hydrochloride (pH 8), concentrated by centircon units (Amicon Corp., Oakville, Ontario, Canada), stored at 4° C., and designated as the periplasmic protein preparation. The cell pellet was suspended in 10 ml of 0.01M Tris hydrochloride (pH 8), sonicated at 100 W for 1 min, and centrifuged at 100,000 × g for 1 h at 4° C. The sonicated supernatant recovered was designated as the cellular protein preparation. The enzymes cyclic phosphodiesterase and beta-galactosidase were assayed as markers for periplasmic and cellular proteins, respectively, as described previously (Neu, H. C., and L. A. Heppel. 1965. The release of enzymes from *Escherichia coli* by osmotic shock and during the formation of spheroplasts. J. Biol. Chem. 240:3685–3692). The protein concentrations of the preparations were determined by the method of Lowry (1951. Protein measurement with the Folin phenol reagent. J. Biol. Chem. 193:265–275).

PROCEDURE 5

SDS-Polyacrylamide Gel Electrophoresis and Western Blot Analysis

The periplasmic and cellular proteins from the *E. coli* recombinant clones were analyzed by SDS-polyacrylamide gel electrophoresis by the method of Hancock and Cary (1979. Outer membrane of *Pseudomonas aeruginosa*: heat- and 2-mercaptoethanol-modifiable proteins. J. Bacteriol. 140:902–910). The separating gel consisted of 9% (wt/vol) acrylamide (acrylamide/bisacrylamide ratio, 40:0.8) in 0.4M Tris hydrochloride (pH 8.8), 0.09M NaCl-1% SDS, while the stacking gel consisted of 3% (wt/vol) acrylamide (acrylamide/bisacrylamide ratio, 20:0.8) in 0.13M Tris hydrochloride (pH 7), 1% SDS. For each lane, approximately 15 μg of protein was mixed with the solubilization reduction mixture (Hancock, R. E. W., and A. M Carey. 1979. Outer membrane of *Pseudomonas aeruginosa*: heat- and 2-mercaptoethanol-modifiable proteins. J. Bacteriol. 140:902–910) and electrophoresed at 150 V with 0.025M Tris, 0.2M glycine (pH 8.4), 1% SDS as the running buffer. Protein bands were visualized by staining the 0.05% Coomassie blue R250 (wt/vol) in 10% acetic acid 14% methanol.

For Western blot analysis (Burnette, W. N. 1981. "Western blotting": electrophoretic transfer of proteins from sodium dodecyl sulfate-polyacrylamide gels to unmodified nitrocellulose and radiographic detection with antibody and radioiodinated protein A. Anal. Biochem. 112:195–203), the proteins were transferred to nitrocellulose paper after SDS-polyacrylamide gel electrophoresis in a Trans-Blot blotting cell apparatus (Bio-Rad) with 0.025M Tris, 0.2M glycine (pH 8.4), 20% methanol as the blotting buffer. The *P. haemolytica* proteins were then detected by ELISA with the rabbit antiserum preparation described above.

PROCEDURE 6

Evaluation of Leukotoxic Activity

The leukotoxic activities of periplasmic and cellular protein preparations were measured in a microplate cytotoxicity assay C. N. Greer and P. E. Shewen "Automated Colourimetric Assay for Detection of *Pasteurella haemolytica* Leukotoxin", Vet. Micro. 12, 31–42, 1986 with BL-3 cells, a bovine leukemia-derived B-lymphocyte cell line (originally obtained from G. Theilen, University of California, Davis), as targets. Cell viability, measured as the uptake of the vital dye neutral red, was determined by reading the optical density of each well at 540 nm with an automated spectrophotometer. After overnight dialysis against RPMI 1640 medium, quadruplicate 200-μl samples (at protein concentrations of 6 mg/ml) were incubated with $2 \times 10^5$ cell in each of four wells of a microtiter plate for 1 h at 37° C. Lyophilized *P. haemolytica* culture supernatant (Shewen, P. E., and B. N. Wilkie. 1982. Cytotoxin of *Pasteurella haemolytica* acting on bovine leukocytes. Infec. Immun. 35:91–94), reconstituted at 3 mg/ml in RPMI 1640 medium, was used as the positive control for toxic activity. Percent toxicity was calculated as the percent loss of viability by comparing the mean optical density in test wells with that in control wells containing cells incubated with RPMI 1640 medium only. The heat liability of toxic activity was determined by preheating an aliquot of each sample at 56° C. for 30 min. before testing. Host species specificity in toxic activity was confirmed by retesting toxic samples with canine, porcine, and human peripheral blood lymphocytes purified by density gradient centrifugation on Ficoll-Hypaque (Shimizu, M., I. C. Pan, and W. R. Hess. 1976. T and B lymphocytes in porcine blood. Am. J. Vet. Res. 36:309–317) as targets. In addition, the rabbit antiserum and a bovine serum with antitoxic activity, obtained from an infected calf, were tested in serial twofold dilutions for the ability to neutralize toxicity in one of the clone-derived samples.

In accordance with the above procedures the following methodology was used to achieve the results noted with reference to the following figures.

METHOD NO. 1

Construction of a Clone Bank of P. haemolytica

About $4 \times 10^3$ E. coli colonies were recovered after transformation with the P. haemolytica DNA fragments and the pBR322 DNA ligation mixture, of which less than 1% were also tetracycline resistant. The transformants were pooled from the agar plates and amplified in broth cultures in LT medium containing ampicillin, and plasmid DNA was prepared by cesium chloride-ethidium bromide centrifugation for storage ($-20°$ C.) as the clone bank. Plasmid DNA of the clone bank was analyzed by agarose gel electrophoresis, which showed that it contained plasmids larger than the vector pBR322. In FIG. 1 lane a is plasmid vector pBR322; lane b is plasmid DNA from the P. haemolytica clone bank. Shown are covalently closed circular (ccc), and (oc) open circular forms of pBR322.

METHOD NO. 2

Isolation of Recombinant Plasmids Coding the P. haemolytica Soluble Antigens Plasmids DNA from the clone bank was transformed into E. coli competent cells, and the transformants were screened for P. haemolytica antigens by the colony ELISA blot method to detect the production of P. haemolytica antigens, Lo and Cameron, (supra). Twenty-seven positive recombinants were identified. Periplasmic and cellular proteins were prepared from the positive clones to assay for the P. haemolytica leukotoxin.

METHOD NO. 3

Characterization of the Recombinant Plasmids

Plasmid DNA from the positive recombinant clones was analyzed by restriction endonuclease mapping, and the results indicated that some of the recombinant plasmids had the same insert DNA. Four recombinant plasmids, 10, 11, 16, and 18, were found to have the same restriction map in that a 6.3-kilobase-pair (kbp) insert was cloned in the vector pBR322 as shown in FIG. 2. The heavy lines represent pBR322 sequences and light lines represent insert sequences.
(a) Plasmid pBR322 is represented linearly at the coordinates of 3 kdbp
(b) Recombinant plasmids pPH 5 and pPH 6
(c) Recombinant plasmids pPH 10, pPH 11, pPH 16, and pPH 18

Figure 3:
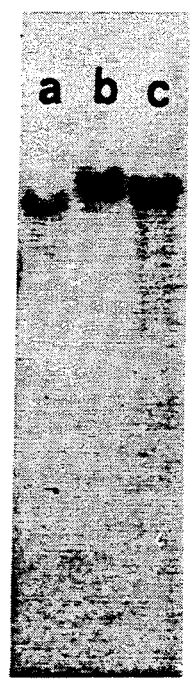
FIG. 3 is a Southern blot hybridization analysis of insert DNA from the plasmid pPH5 against total *Pasteurella haemolytica* genomic DNA.

The nomenclature used in FIG. 2 has the following meaning:
P is equivalent to restriction site PstI
H is equivalent to restriction site HincII
C is equivalent to restriction site ClaI
A is equivalent to restriction site AvaI
PI is equivalent to restriction site PvuI
B is equivalent to restriction site BamHI
PII is equivalent to restriction site PvuII
B/S is equivalent to restriction site BamHI-Sau3A junctions In this restriction mapping there are no restriction sites for the endonucleases on the insert DNA of EcoRI, BamHI, HindIII, SalI, NdeI, KpnI, SmaI and XbaI. More interestingly, the same 6.3-kbp insert DNA was also cloned in plasmids 5 and 6 in the opposite orientation (as shown in FIG. 3).

To demonstrate that the insert DNA was of P. haemolytica origin, the PstI-AvaI fragment from plasmid 5 was purified, nick-translated with [alpha-$^{32}$P]dATP, and used as a probe in Southern blot analysis against P. haemolytica genomic DNA. The results (shown in FIG. 3) indicate that the insert DNA hybridized to unique fragments of the P. haemolytica DNA digest.

METHOD 4

Testing for the P. haemolytic Leukotoxin in the E. coli Recombinant Clones

Periplasmic and cellular proteins from the E. coli clones carrying the recombinant plasmids 1, 5, 8, 9, 10, 11 and 13 as well as plasmid pBR322 were assayed for leukotoxin activity. None of the periplasmic protein preparations shows significant cytotoxic activity. Cellular proteins recovered after sonication from three recombinant clones were found to be toxic for BL-3 cells. These were clones carrying plasmids 5, 10, and 11, which showed 95.5, 53.1, and 55.5% toxicity, respectively. For plasmids 10 and 11, all activity was heat labile (56° C., 1 h), while 26.1% of the toxicity in the plasmid 5 preparation was heat stable. In comparison, the P. haemolytica culture supernatant (Shewen, P. E., and B. N. Wilkie. 1982. Cytotoxin of Pasteurella haemolytica acting on bovine leukocytes. Infec. Immun. 35:91–94) used as a toxicity control was 93.4% and 19.6% toxic after heating.

Cellular proteins from the clone bearing plasmid 5 showed no toxicity for canine, porcine or human peripheral blood lymphocites when tested. Likewise, the P. haemolytica control was not toxic for these non-ruminant cells.

Both bovine and rabbit antitoxic sera neutralized the toxic activity of cellular proteins from the clone bearing plasmid 5 at a 1/256 dilution, the highest dilution tested. No neutralization occurred at any dilution with the normal rabbit serum pool or the fetal calf serum pool, which were used as controls.

METHOD 5

SDS-Polyacrylamide Gel Electrophoresis and Western Blot Analysis

Figure 4:
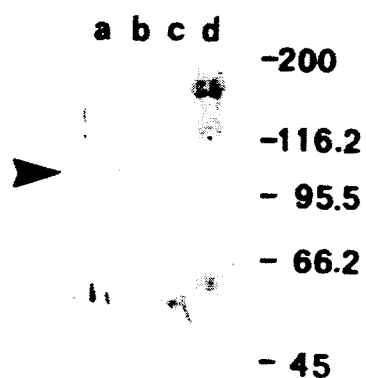
FIG. 4 is a Western blot analysis of the cellular proteins from the *E. coli* clones carrying pPH5, pPH10 and the vector pBR322.

The protein preparations from the recombinant clones carrying plasmid 5 and plasmid 10 were analyzed by SDS-polyacrylamide gel electrophoresis followed by electrophoretic transfer to nitrocellulose paper and ELISA. Results from Coomassie blue staining of the gels indicated no new protein bands in the periplasmic protein preparations. However, an additional protein band was detected after Western blot analysis of the cellular protein preparation from the recombinant clone carrying plasmid 5 (as shown in FIG. 4). This additional protein band migrated to a position which corresponds to one of the soluble antigens in the P. haemolytica culture supernatant. The molecular weight of the extra protein was estimated to be about 100,000.

In the Western blot analysis (as shown in FIG. 4), several other bands were detected in all of the protein preparations. Since these bands were present also in the control sample, E. coli carrying pBR322, they are probably E. coli proteins which react with the antibody preparation and do not affect the present interpretation.

With reference to FIG. 5, the plasmid pPH5 is one of the recombinant plasmids isolated in accordance with the above procedures. Upon further characterization of the insert DNA of pPH5 by DNA sequencing analysis it became apparent that two open reading frames ($ORF_1$ and $ORF^2$) were identified. It was found, however, that the $ORF^1$ was incomplete in that it was lacking a termination signal. By subsequent probing of the P. haemolytica A1 clone bank a second plasmid pPH5A was recovered. Such probe was accomplished on the basis of using the 1.7 kbp BamHI-PstI fragment from the pPH5 DNA sequence which was purified and used as a probe to screen the P. haemolytica A1 bank. This plasmid contains insert sequences further to the left of the BamHI site on the pPH5. With reference to FIG. 5, however, the pPH5A was lacking sequences to the right of the PvuI site on the pPH5 sequence. The sequence from the PvuI site to EcoRV on the pPH5 was determined to be part of the coding region of $ORF_2$. From this information a new plasmid was constructed using sequences from pPH5 and pPH5A to produce the plasmid pLKT5. This plasmid contains all the insert sequences covering the regions of $ORF_2$ and $ORF_1$. The legend for FIG. 5 is as follows:

P is equivalent to the restriction site PstI
$P_1$ is equivalent to the restriction site PvuI
H is equivalent to the restriction site HincIII
Ev is equivalent to the restriction site EcoRV
B is equivalent to the restriction site BamHI
$P_2$ is equivalent to the restriction site PvuII
BII is equivalent to the restriction site BglII
B/S is equivalent to the restriction site BamHI-Sau3A junction The $ORF_2$ is a coding sequence of 498 nucleotides which codes for 166 amino acids. The deduced molecular weight then of the resultant protein is 19,820 daltons. $ORF_1$ is a coding sequence of 2856 nucleotides which in turn codes for protein having 952 amino acid groups with a deduced molecular weight of 101,883 daltons. This is the leukotoxin which is produced on expression of the plasmid pLKT5 in the suitable host micro-organism such as *E. coli.*

The identifying characteristics of pBR322 and *E. coli* HB101 are already reported as noted above. The leukotoxin gene as found in the recombinant plasmid pLKT4 and as transferred in host *E. coli* HB101 is characterized as deposited at ATCC, deposition No. 68025.

When the protein preparations from a number of the *E. coli* recombinant clones were assayed for leukotoxic activity, three preparations were found to be toxic for the BL-3 cells. These were the cellular proteins from the clones carrying plasmids 5, 10, and 11. Interestingly, they all carried the same *P. haemolytica* insert DNA in either of the two orientations (FIG. 2). After the initial toxicity assay, three more recombinant plasmids, 6, 16 and 18, were also identified as carrying the same insert DNA. These results suggest that the leukotoxinc gene is carried on the 6.3-kbp insert DNA. Furthermore, the 6.3-kbp DNA must also carry the necessary regulatory regions for the expression of the leukotoxin.

The leukotoxic activity of these protein preparations was heat labile, which is characteristic of the *P. haemolytica* leukotoxin. Furthermore, similar to the *P. haemolytica* leukotoxin, the preparation from the recombinant clones carrying pPH5 was found to be non-toxic for canine, porcine, and human peripheral blood lymphocytes (Shewen, P. E., and B. M. Wilkie. 1982. Cytotoxin of *Pasteurella haemolytica* acting on bovine leukocytes. Infect. Immun. 35:91–94). In addition, both rabbit and bovine antitoxic sera neutralized the toxicity in the pPH5 preparation. Therefore, the *P. haemolytica* leukotoxin gene is carried in this 6.3-kbp DNA fragment. Results from Southern blot analysis, in which the insert DNA hybridized to unique DNA fragments of the *P. haemolytica* genome, indicate that there is only one copy of the leukotoxin gene in *P. haemolytica.*

The leukotoxic activity of the protein preparation from the *E. coli* clones carrying pPH5 was found to be twice that of the protein preparations from the clones carrying pPH10 and pPH11. Furthermore, an additional protein band was found in the pPH5 protein preparation after Western blot analysis (FIG. 4). This additional band was absent in the pPH10 and the control pBR322 protein preparations. We suggest that there is a higher level of leukotoxin produced when the 6.3-kbp insert DNA is cloned in the orientation seen in pPH5. This increased level of leukotoxin production may be a result of expression from both the leukotoxin promoter and the tetracycline promoter on pBR322 in pPH5, while in the other orientation, i.e., pPH10, the leukotoxin can be expressed only from its own promoter.

The migration of the *P. haemolytica* leukotoxin produced in the *E. coli* recombinant clone carrying pPH5 during SDS-polyacrylamide gel electrophoresis corresponded to one of the soluble antigens present in the *P. haemolytica* culture supernatant (FIG. 4), confirming that the molecular weight of the leukotoxin is about 100,000. Other researchers, by using physical techniques for purification, have reported molecular weights for the *P. haemolytica* leukotoxin of 150,000 (Himmel, M. E., M.D. Yates, L. H. Lauerman, and P. G. Squire, 1982. Purification and partial characterization of a macrophage cytotoxin from *Pasteurella haemolytica*. Am. J. Vet. Res. 43:764–767) and 300,000 (Baluyut, C. S., R. R. Simonson, W. J. Bemrick, and S. K. Maheswaran. 1981. Interaction of *Pasteurella haemolytica* with bovine neutrophils: identification and partial characterization of cytotoxin. Am. J. Vet. Res. 42:1920–1926). These may be overestimated due to the aggregation of binding of serum materials with the leukotoxin. A more accurate determination of the molecular weight of the leukotoxin is possible from the DNA sequence anlaysis of the cloned gene.

During the initial screening of leukotoxic activity from the recombinant clones, toxic activities were observed only with the cellular protein preparations from *E. coli* containing pPH5, pPH10 or pPH11. No leukotoxic activity was found in the respective periplasmic protein preparations. The failure of the *P. haemolytica* leukotoxin to be excreted by the *E. coli* cells is not unexpected since it has been observed on a number of occasions that foreign proteins produced in *E. coli* from cloned genes were not exported (Coleman, K., G. Dougan, and J. P. Arbuthnott. 1983. Cloning and expression in *Escherichia coli* K-12, of the chromosomal hemolysin (phospholipase C) determinant of Pseudomonas aeruginosa, J. Bacteriol. 153:909–915); (Gray, G. L., D. H. Smith, J. S. Baldridge, R. N. Haskins, M. L. Vasil, E. Y.

Chen, and H. L. Heyneker. 1984. Cloning, nucleotide sequence and expression in *Escherichia coli* of the exotoxin A structural gene of *Pseudomonas aeruginosa*. Proc. Natl. Acad. Sci. USA 81:2645-2649).

By way of DNA sequencing analysis in accordance with standard procedures, the nucleotide sequence of ORF₁ and ORF₂ is as follows:

The sequence is numbered from −469 at the rightmost EcoRV site of FIG. 5 on the pLKT5 plasmid and counting leftward. Nucleotide No. 1 is the first nucleotide of the coding region of ORF₂ at approximately nucleotide 510 there is the break between ORF₂ and ORF₁.

```
                    LEUKOTOXIN GENES Reads from EcoRV through PvuI
   -469        -460        -450        -440        -430        -420
GATATCTTG  TGCCTGCGCA  GTAACCACAC  ACCCGAATAA  AAGGGTCAAA  AGTGTTTTTT -410        -400        -390        -380        -370        -360
TCATAAAAAG  TCCCTGTGTT  TTCATTATAA  GGATTACCAC  TTTAACGCAG  TTACTTTCTT -350        -340        -330        -320        -310        -300
AAAAAAAGTC  TTCTTTTCAT  AAAGTTTGTT  TTATGTCATA  CAAACACATC  AAATTGAGTA -290        -280        -270        -260        -250        -240
GTAGTTTCTC  AATCCTCTTG  ATTCCTCTAT  CTCAAAAAAA  CAACCCAAAA  GAAAAAAGAA -230        -220        -210        -200        -190        -180
AAGTATATGT  TACATTAATA  TTACAATGTA  ATTATTTTGT  TTAATTTCCC  TACATTTTGT -170        -160        -150        -140        -130        -120
ATAACTTTAA  AACACTCCTT  TTTCTCTTCT  GATTATATAA  AAGACAAAAA  ATACAATTTA -110        -100         -90         -80         -70         -60
AGCTACAAAA  AACAACAAAA  AACAACAAAA  AACACGACAA  TAAGATCGAG  TAATGATTAT -50         -40         -30         -20         -10
ATTATGTTAT  AATTTTTGAC  CTAATTTAGA  ATAATTATCG  AGTGCAAATT  ATG AAT CAA
                                                            Met Asn Gln 15                  30                  45                  60
TCT TAT TTT AAC TTA CTA GGA AAC ATT ACT TGG CTA TGG ATG AAC TCC TCC CTC
Ser Tyr Phe Asn Leu Leu Gly Asn Ile Thr Trp Leu Trp Met Asn Ser Ser Leu 75                  90                 105
CAC AAA GAA TGG AGC TGT GAA CTA CTA GCA CGC AAT GTG ATT CCT GCA ATT GAA
His Lys Glu Trp Ser Cys Glu Leu Leu Ala Arg Asn Val Ile Pro Ala Ile Glu 120                 135                 150                 165
AAT GAA CAA TAT ATG CTA CTT ATA GAT AAC GGT ATT CCG ATC GCT TAT TGT AGT
Asn Glu Gln Tyr Met Leu Leu Ile Asp Asn Gly Ile Pro Ile Ala Tyr Cys Ser 180                 195                 210                 225
TGG GCA GAT TTA AAC CTT GAG ACT GAG GTG AAA TAT ATT AAG GAT ATT AAT TCG
Trp Ala Asp Leu Asn Leu Glu Thr Glu Val Lys Tyr Ile Lys Asp Ile Asn Ser 240                 255                 270
TTA ACA CCA GAA GAA TGG CAG TCT GGT GAC AGA CGC TGG ATT ATT GAT TGG GTA
Leu Thr Pro Glu Glu Trp Gln Ser Gly Asp Arg Arg Trp Ile Ile Asp Trp Val 285                 300                 315                 330
GCA CCA TTC GGA CAT TCT CAA TTA CTT TAT AAAAAA ATG TGT CAG AAA TAC CCT
Ala Pro Phe Gly His Ser Gln Leu Leu Tyr Lys Lys Met Cys Gln Lys Tyr Pro 345                 360                 375
GAT ATG ATC GTC AGA TCT ATA CGC TTT TAT CCA AAG CAG AAA GAA TTA GGC AAA
Asp Met Ile Val Arg Ser Ile Arg Phe Tyr Pro Lys Gln Lys Glu Leu Gly Lys 390                 405                 420                 435
ATT GCC TAC TTT AAA GGA GGT AAA TTA GAT AAA AAA ACA GCA AAA AAA CGT TTT
Ile Ala Tyr Phe Lys Gly Gly Lys Leu Asp Lys Lys Thr Ala Lys Lys Arg Phe 450                 465                 480                 495
GAT ACA TAT CAA GAA GAG CTG GCA ACA GCA CTT AAA AAT GAA TTT AAT TTT ATT
Asp Thr Tyr Gln Glu Glu Leu Ala Thr Ala Leu Lys Asn Glu Phe Asn Phe Ile 510     519     525                 540
AAA AAA TAG AAGGAG ACATCCCTT ATG GGA ACT AGA CTT ACA ACC CTA TCA AAT
Lys Lys  *                  Met Gly Thr Arg Leu Thr Thr Leu Ser Asn 555                 570                 585                 600
GGG CTA AAA AAC ACT TTA ACG GCA ACC AAA AGT GGC TTA CAT AAA GCC GGT CAA
Gly Leu Lys Asn Thr Leu Thr Ala Thr Lys Ser Gly Leu His Lys Ala Gly Gln 615                  630                 645
TCA TTA ACC CAA GCC GGC AGT TCT TTA AAA ACT GGG GCA AAA AAA ATT ATC CTC
Ser Leu Thr Gln Ala Gly Ser Ser Leu Lys Thr Gly Ala Lys Lys Ile Ile Leu
```

```
660                     675                          690                          705
TAT ATT CCC CAA AAT TAC CAA TAT GAT ACT GAA CAA GGT AAT GGT TTA CAG GAT
Tyr Ile Pro Gln Asn Tyr Gln Tyr Asp Thr Glu Gln Gly Asn Gly Leu Gln Asp 720                          735                          750                     765
TTA GTC AAA GCG GCC GAA GAG TTG GGG ATT GAG GTA CAA AGA GAA GAA CGC AAT
Leu Val Lys Ala Ala Glu Glu Leu Gly Ile Glu Val Gln Arg Glu Glu Arg Asn 780                          795                          810
AAT ATT GCA ACA GCT CAA ACC AGT TTA GGC ACG ATT CAA ACC GCT ATT GGC TTA
Asn Ile Ala Thr Ala Gln Thr Ser Leu Gly Thr Ile Gln Thr Ala Ile Gly Leu 825                          840                          855                     870
ACT GAG CGT GGC ATT GTG TTA TCC GCT CCA CAA ATT GAT AAA TTG CTA CAG AAA
Thr Glu Arg Gly Ile Val Leu Ser Ala Pro Gln Ile Asp Lys Leu Leu Gln Lys 885                          900                          915
ACT AAA GCA GGC CAA GCA TTA GGT TCT GCC GAA AGC ATT GTA CAA AAT GCA AAT
Thr Lys Ala Gly Gln Ala Leu Gly Ser Ala Glu Ser Ile Val Gln Asn Ala Asn 930                     945                          960                     975
AAA GCC AAA ACT GTA TTA TCT GGC ATT CAA TCT ATT TTA GGC TCA GTA TTG GCT
Lys Ala Lys Thr Val Leu Ser Gly Ile Gln Ser Ile Leu Gly Ser Val Leu Ala 990                          1005                         1020                    1035
GGA ATG GAT TTA GAT GAG GCC TTA CAG AAT AAC AGC AAC CAA CAT GCT CTT GCT
Gly Met Asp Leu Asp Glu Ala Leu Gln Asn Asn Ser Asn Gln His Ala Leu Ala 1050                         1065                         1080
AAA GCT GGC TTG GAG CTA ACA AAT TCA TTA ATT GAA AAT ATT GCT AAT TCA GTA
Lys Ala Gly Leu Glu Leu Thr Asn Ser Leu Ile Glu Asn Ile Ala Asn Ser Val 1095                         1110                         1125                    1140
AAA ACA CTT GAC GAA TTT GGT GAG CAA ATT AGT CAA TTT GGT TCA AAA CTA CAA
Lys Thr Leu Asp Glu Phe Gly Glu Gln Ile Ser Gln Phe Gly Ser Lys Leu Gln 1155                         1170                         1185
AAT ATC AAA GGC TTA GGG ACT TTA GGA GAC AAA CTC AAA AAT ATC GGT GGA CTT
Asn Ile Lys Gly Leu Gly Thr Leu Gly Asp Lys Leu Lys Asn Ile Gly Gly Leu 1200                    1215                         1230                    1245
GAT AAA GCT GGC CTT GGT TTA GAT GTT ATC TCA GGG CTA TTA TCG GGC GCA ACA
Asp Lys Ala Gly Leu Gly Leu Asp Val Ile Ser Gly Leu Leu Ser Gly Ala Thr 1260                         1275                         1290                    1305
GCT GCA CTT GTA CTT GCA GAT AAA AAT GCT TCA ACA GCT AAA AAA GTG GGT GCG
Ala Ala Leu Val Leu Ala Asp Lys Asn Ala Ser Thr Ala Lys Lys Val Gly Ala 1320                         1335                         1350
GGT TTT GAA TTG GCA AAC CAA CTT GTT GGT AAT ATT ACC AAA GCC GTT TCT TCT
Gly Phe Glu Leu Ala Asn Gln Leu Val Gly Asn Ile Thr Lys Ala Val Ser Ser 1365                         1380                         1395                    1410
TAC ATT TTA GCC CAA CGT GTT GCA GCA GGT TTA TCT TCA ACT GGG CCT GTG GCT
Tyr Ile Leu Ala Gln Arg Val Ala Ala Gly Leu Ser Ser Thr Gly Pro Val Ala 1425                         1440                         1455
GCT TTA ATT GCT TCT ACT GTT TCT CTT GCG ATT AGC CCA TTA GCA TTT GCC GGT
Ala Leu Ile Ala Ser Thr Val Ser Leu Ala Ile Ser Pro Leu Ala Phe Ala Gly 1470                    1485                         1500                    1515
ATT GCC GAT AAA TTT AAT CAT GCA AAA AGT TTA GAG AGT TAT GCC GAA CGC TTT
Ile Ala Asp Lys Phe Asn His Ala Lys Ser Leu Glu Ser Tyr Ala Glu Arg Phe 1530                         1545                         1560                    1575
AAA AAA TTA GGC TAT GAC GGA GAT AAT TTA TTA GCA GAA TAT CAG CGG GGA ACA
Lys Lys Leu Gly Tyr Asp Gly Asp Asn Leu Leu Ala Glu Tyr Gln Arg Gly Thr 1590                         1605                         1620
GGG ACT ATT GAT GCA TCG GTT ACT GCA ATT AAT ACC GCA TTG GCC GCT ATT GCT
Gly Thr Ile Asp Ala Ser Val Thr Ala Ile Asn Thr Ala Leu Ala Ala Ile Ala 1635                         1650                         1665                    1680
GGT GGT GTG TCT GCT GCT GCA GCC GGC TCG GTT ATT GCT TCA CCG ATT GCC TTA
Gly Gly Val Ser Ala Ala Ala Ala Gly Ser Val Ile Ala Ser Pro Ile Ala Leu 1695                         1710                         1725
TTA GTA TCT GGG ATT ACC GGT GTA ATT TCT ACG ATT CTG CAA TAT TCT AAA CAA
Leu Val Ser Gly Ile Thr Gly Val Ile Ser Thr Ile Leu Gln Tyr Ser Lys Gln
```

-continued

```
1740                   1755                   1770                   1785
GCA ATG TTT GAG CAC GTT GCA AAT AAA ATT CAT AAC AAA ATT GTA GAA TGG GAA
Ala Met Phe Glu His Val Ala Asn Lys Ile His Asn Lys Ile Val Glu Trp Glu 1800                   1815                   1830                   1845
AAA AAT AAT CAC GGT AAG AAC TAC TTT GAA AAT GGT TAC GAT GCC CGT TAT CTT
Lys Asn Asn His Gly Lys Asn Tyr Phe Glu Asn Gly Tyr Asp Ala Arg Tyr Leu 1860                   1875                   1890
GCG AAT TTA CAA GAT AAT ATG AAA TTC TTA CTG AAC TTA AAC AAA GAG TTA CAG
Ala Asn Leu Gln Asp Asn Met Lys Phe Leu Leu Asn Leu Asn Lys Glu Leu Gln 1905                   1920                   1935                   1950
GCA GAA GCT GTC ATC GCT ATT ACT CAG CAG CAA TGG GAT AAC AAC ATT GGT GAT
Ala Glu Arg Val Ile Ala Ile Thr Gln Gln Gln Trp Asp Asn Asn Ile Gly Asp 1965                   1980                   1995
TTA GCT GGT ATT AGC CGT TTA GGT GAA AAA GTC CTT AGT GGT AAA GCC TAT GTG
Leu Ala Gly Ile Ser Arg Leu Gly Glu Lys Val Leu Ser Gly Lys Ala Tyr Val 2010                   2025                   2040                   2055
CAT CCG TTT GAA GAA GGC AAA CAC ATT AAA GCC GAT AAA TTA GTA CAG TTG GAT
Asp Ala Phe Glu Glu Gly Lys His Ile Lys Ala Asp Lys Leu Val Gln Leu Asp 2070                   2085                   2100                   2115
TCG GCA AAC GGT ATT ATT GAT GTG AGT AAT TCG GGT AAA GCG AAA ACT CAG CAT
Ser Ala Asn Gly Ile Ile Asp Val Ser Asn Ser Gly Lys Ala Lys Thr Gln His 2130                   2145                   2160
ATC TTA TTC AGA ACG CCA TTA TTG ACG CCG GGA ACA GAG CAT CGT GAA CGC GTA
Ile Leu Phe Arg Thr Pro Leu Leu Thr Pro Gly Thr Glu His Arg Glu Arg Val 2175                   2190                   2205                   2220
CAA ACA GGT AAA TAT GAA TAT ATT ACC AAG CTC AAT ATT AAC CGT GTA GAT AGC
Glu Thr Gly Lys Tyr Glu Tyr Ile Thr Lys Leu Asn Ile Asn Arg Val Asp Ser 2235                   2250                   2265
TGG AAA ATT ACA GAT GGT GCA GCA AGT TCT ACC TTT GAT TTA ACT AAC GTT GTT
Trp Lys Ile Thr Asp Gly Ala Ala Ser Ser Thr Phe Asp Leu Thr Asn Val Val 2280                   2295                   2310                   2325
CAG CGT ATT GGT ATT GAA TTA GAC AAT GCT GGA AAT GTA ACT AAA ACC AAA GAA
Gln Arg Ile Gly Ile Glu Leu Asp Asn Ala Gly Asn Val Thr Lys Thr Lys Glu 2340                   2355                   2370                   2385
ACA AAA ATT ATT GCC AAA CTT GGT GAA GGT GAT GAC AAC GTA TTT GTT GGT TCT
Thr Lys Ile Ile Ala Lys Leu Gly Glu Gly Asp Asp Asn Val Phe Val Gly Ser 2400                   2415                   2430
GGT ACG ACG GAA ATT GAT GGC GGT GAA GGT TAC GAC CGA GTT CAC TAT AGC CGT
Gly Thr Thr Glu Ile Asp Gly Gly Glu Gly Tyr Asp Arg Val His Tyr Ser Arg 2445                   2460                   2475                   2490
GGA AAC TAT GGT GCT TTA ACT ATT GAT GCA ACC AAA GAG ACC GAG CAA GGT AGT
Gly Asn Tyr Gly Ala Leu Thr Ile Asp Ala Thr Lys Glu Thr Glu Gln Gly Ser 2505                   2520                   2535
TAT ACC GTA AAT CGT TTC GTA GAA ACC GGT AAA GCA CTA CAC GAA GTG ACT TCA
Tyr Thr Val Asn Arg Phe Val Glu Thr Gly Lys Ala Leu His Glu Val Thr Ser 2550                   2565                   2580                   2595
ACC CAT ACC GCA TTA GTG GGC AAC CGT GAA GAA AAA ATA GAA TAT CGT CAT AGC
Thr His Thr Ala Leu Val Gly Asn Arg Glu Glu Lys Ile Glu Tyr Arg His Ser 2610                   2625                   2640                   2655
AAT AAC CAG CAC CAT GCC GGT TAT TAC ACC AAA GAT ACC TTG AAA GCT GTT GAA
Asn Asn Gln His His Ala Gly Tyr Tyr Thr Lys Asp Thr Leu Lys Ala Val Glu 2670                   2685                   2700
GAA ATT ATC GGT ACA TCA CAT AAC GAT ATC TTT AAA GGT AGT AAG TTC AAT GAT
Glu Ile Ile Gly Thr Ser His Asn Asp Ile Phe Lys Gly Ser Lys Phe Asn Asp 2715                   2730                   2745                   2760
GCC TTT AAC GGT GGT GAT GGT GTC GAT ACT ATT GAC GGT AAC GAC GGC AAT GAC
Ala Phe Asn Gly Gly Asp Gly Val Asp Thr Ile Asp Gly Asn Asp Gly Asn Asp 2775                   2790                   2805
CGC TTA TTT GGT GGT AAA GGC GAT GAT ATT CTC GAT GGT GGA AAT GGT GAT GAT
Arg Leu Phe Gly Gly Lys Gly Asp Asp Ile Leu Asp Gly Gly Asn Gly Asp Asp
```

```
2820                    2835                    2850                         2865
TTT ATC GAT GGC GGT AAA GGC AAC GAC CTA TTA CAC GGT GGC AAG GGC GAT GAT
Phe Ile Asp Gly Gly Lys Gly Asn Asp Leu Leu His Gly Gly Lys Gly Asp Asp 2880                    2895                    2910                    2925
ATT TTC GTT CAC CGT AAA GGC GAT GGT AAT GAT ATT ATT ACC GAT TCT GAC GGC
Ile Phe Val His Arg Lys Gly Asp Gly Asn Asp Ile Ile Thr Asp Ser Asp Gly 2940                     2955                    2970
AAT GAT AAA TTA TCA TTC TCT GAT TCG AAC TTA AAA GAT TTA ACA TTT GAA AAA
Asn Asp Lys Leu Ser Phe Ser Asp Ser Asn Leu Lys Asp Leu Thr Phe Glu Lys 2985                    3000                    3015                         3030
GTT AAA CAT AAT CTT GTC ATC ACG AAT AGC AAA AAA GAG AAA GTG ACC ATT CAA
Val Lys His Asn Leu Val Ile Thr Asn Ser Lys Lys Glu Lys Val Thr Ile Gln 3045                    3060                    3075
AAC TGG TTC CGA GAG GCT GAT TTT GCT AAA GAA GTG CCT AAT TAT AAA GCA ACT
Asn Trp Phe Arg Glu Ala Asp Phe Ala Lys Glu Val Pro Asn Tyr Lys Ala Thr 3090                    3105                    3120                    3135
AAA GAT GAG AAA ATC GAA GAA ATC ATC GGT CAA AAT GGC GAG CGG ATC ACC TCA
Lys Asp Glu Lys Ile Glu Glu Ile Ile Gly Gln Asn Gly Glu Arg Ile Thr Ser 3150                    3165                    3180                    3195
AAG CAA GTT GAT GAT CTT ATC GCA AAA GGT AAC GGC AAA ATT ACC CAA GAT GAG
Lys Gln Val Asp Asp Leu Ile Ala Lys Gly Asn Gly Lys Ile Thr Gln Asp Glu 3210                    3225                    3240
CTA TCA AAA GTT GTT GAT AAC TAT GAA TTG CTC AAA CAT AGC AAA AAT GTG ACA
Leu Ser Lys Val Val Asp Asn Tyr Glu Leu Leu Lys His Ser Lys Asn Val Thr 3255                    3270                    3285                    3300
AAC AGC TTA GAT AAG TTA ATC TCA TCT GTA AGT GCA TTT ACC TCG TCT AAT GAT
Asn Ser Leu Asp Lys Leu Ile Ser Ser Val Ser Ala Phe Thr Ser Ser Asn Asp 3315                    3330                    3345
TCG AGA AAT GTA TTA GTG GCT CCA ACT TCA ATG TTG GAT CAA AGT TTA TCT TCT
Ser Arg Asn Val Leu Val Ala Pro Thr Ser Met Leu Asp Gln Ser Leu Ser Ser 3360                    3375                    3390       3400            3410
CTT CAA TTT GCT AGA GCA GCT TAA TTTTTAATG ATTGGCAACT CTATATTGTT
Leu Gln Phe Ala Arg Ala Ala  *

3420        3430        3440        3450        3460        3470
TCACACATTA TAGAGTTGCC GTTTTATTTT ATAAAAGGAG ACAATATGGA AGCTAACCAT 3480        3490        3500        3510        3520        3530
CAAAGGAATG ATCTTGGTTT AGTTGCCCTC ACTATGTTGG CACAATACCA TAATATTTCG 3540        3550        3560        3570        3580        3590
CTTAATCCGG AAGAAATAAA ACATAAATTT GATCTTGACG GAAAAGGGCT TTCTTTAACT 3600        3610        3620        3630        3640        3650
GCTTGGCTTT TAGCTGCAAA ATCGTTAGCG TTGAAAGCGA AACACATTAA AAAAGCGCTT 3660        3670        3680        3690        3700        3710
TCCCGCTTAC ACTTGGTGAA TTTACCGGCA TTAGTTTGGC AAGATAACGG TAAACATTTT 3720        3730    3734
TTATTGGTAA AAGTGGATAC CGAT
```

Beneath the codons of the DNA sequence, the corresponding amino acid has been identified. It is appreciated that the letters indicating the nucleic acids of the DNA sequence and the expressed amino acids are in accordance with International lettering which is well understood by those skilled in the art.

Having isolated the gene coding for the leukotoxin of P. haemolytica it is appreciated that many steps may be taken in improving animal health care. Based on this information and in the expression of the gene, a suitable vaccine is prepared without the impurities of a vaccine prepared from the culture supernatant. The DNA sequence may be used in its entirety or fragment or fragments thereof as a DNA probe. The expressed leukotoxin protein may be used as the pure antigen in developing poly- and monoclonal antibodies. It is appreciated that the DNA sequence coding for the leukotoxin may be transformed into a suitable host micro-organism by either a suitable plasmid such as pBR322 or a suitable phage lamda.

The suitable host micro-organism such as the E. coli may be cultured under suitable conditions to produce the leukotoxin. The leukotoxin may be isolated from the cells after culture is complete. A sonicated host cell protein preparation can be fractionated by preparative polyacrylamide gel electrophoresis using a denaturing system at pH 9.7 where the leukotoxin has been shown to migrate at a low rate. Using in vivo expression of the leukotoxin in the E. coli mini cell system, the position of the leukotoxin on a non-denaturing system by PAGE and Western blot analysis is achieved. Using the cloned protein, rabbits can be immunized by subcutaneous and intravenous inoculation and evaluated for development of antibodies to the cloned antigen by micro immunodiffusion and dot blot analysis. The antibodies are tested for reactivity with *P. haemolytica* surface antigens by micro-agglutination and for the ability to neutralize the cytotoxin.

In establishing that the cloned leukotoxin antigen proves to be immunogenic in rabbits, tests may then be conducted for immunogenicity and protective capabilities in challenge experiments involving calves. Such analysis establishes the effectiveness of vaccines prepared from the genetically produced leukotoxin against pneumonia in calves.

While preferred embodiments of this invention have been described and illustrated herein, the person skilled in the art will appreciate that changes and modifications may be made therein without departing from the spirit and scope of this invention as defined in the appended claims.

We claim:

1. A substantially pure DNA sequence encoding for leukotoxin which is a protein produced by metabolism of Pasteurella heamolytica, wherein said leukotoxin exhibits cytotoxic activity specific against leukocytes.

2. The substantially pure DNA sequence as claimed in claim 1, wherein said DNA sequence has the restriction site map of plasmid pLKT5 in FIG. 5.

3. The substantially pure DNA sequence as claimed in claim 1, wherein said DNA sequence is approximately 8.7 Kbp in size.

4. The substantially pure DNA sequence as claimed in claim 1, wherein said DNA sequence comprises the following DNA sequence, wherein T represents a thymine nucleotide, G represents a quanine nucleotide, A represents an adenine nucleotide and C represents a cytosine nucleotide:

```
                                        ATG GGA ACT AGA CTT ACA ACC CTA TCA AAT
GGG CTA AAA AAC ACT TTA ACG GCA ACC AAA AGT GGC TTA CAT AAA GCC GGT CAA
TCA TTA ACC CAA GCC GGC AGT TCT TTA AAA ACT GGG GCA AAA AAA ATT ATC CTC
TAT ATT CCC CAA AAT TAC CAA TAT GAT ACT GAA CAA GGT AAT GGT TTA CAG GAT
TTA GTC AAA GCG GCC GAA GAG TTG GGG ATT GAG GTA CAA AGA GAA GAA CGC AAT
AAT ATT GCA ACA GCT CAA ACC AGT TTA GGC ACG ATT CAA ACC GCT ATT GGC TTA
ACT GAG CGT GGC ATT GTG TTA TTC GCT CCA CAA ATT GAT AAA TTG CTA CAG AAA
ACT AAA GCA GGC CAA GCA TTA GGT TCT GCC GAA AGC ATT GTA CAA AAT GCA AAT
AAA GCC AAA ACT GTA TTA TCT GGC ATT CAA TCT ATT TTA GGC TCA GTA TTG GCT
GGA ATG GAT TTA GAT GAG GCC TTA CAG AAT AAC AGC AAC CAA CAT GCT CTT GCT
AAA GCT GGC TTG GAG CTA ACA AAT TCA TTA ATT GAA AAT ATT GCT AAT TCA GTA
AAA ACA CTT GAC GAA TTT GGT GAG CAA ATT AGT CAA TTT GGT TCA AAA CTA CAA
AAT ATC AAA GGC TTA GGG ACT TTA GGA GAC AAA CTC AAA AAT ATC GGT GGA CTT
GAT AAA GCT GGC CTT GGT TTA GAT GTT ATC TCA GGG CTA TTA TCG GGC GCA ACA
GCT CCA CTT GTA CTT GCA GAT AAA AAT GCT TCA ACA GCT AAA AAA GTG GGT GCG
GGT TTT GAA TTG GCA AAC CAA GTT GTT GGT AAT ATT ACC AAA GCC GTT TCT TCT
TAC ATT TTA GCC CAA CGT GTT GCA GCA GGT TTA TCT TCA ACT GGG CCT GTG GCT
GCT TTA ATT GCT TCT ACT GTT TCT CTT GCG ATT AGC CCA TTA GCA TTT GCC GGT
ATT GCC GAT AAA TTT AAT CAT GCA AAA AGT TTA GAG AGT TAT GCC GAA CGC TTT
AAA AAA TTA GGC TAT GAC GGA GAT AAT TTA TTA GCA GAA TAT CAG CGG GGA ACA
GGG ACT ATT GAT GCA TCG GTT ACT GCA ATT AAT ACC GCA TTG GCG GCT ATT GCT
CGT GGT GTG TCT GCT GCT GCA GCG GGC TCG GTT ATT GCT TCA CCG ATT GCC TTA
TTA GTA TCT GGGG ATT ACC GGT GTA ATT TCT ACG ATT CTG CAA TAT TCT AAA CAA
GCA ATG TTT GAG CAC GTT GCA AAT AAA ATT CAT AAC AAA ATT GTA GAA TGG GAA
AAA AAT AAT CAC GGT AAG AAC TAC TTT GAA AAT GGT TAC GAT GCC CGT TAT CTT
GCG AAT TTA CAAQ GAT AAT ATG AAA TTC TTA CTG AAC TTA AAC AAA GAG TTA CAG
GCA GAA CGT GTC ATC GCT ATT ACT CAG CAG CAA TGG GAT AAC AAC ATT GGT GAT
TTA GCT GGT ATT AGC CGT TTA GGT GAA AAA GTC CTT AGT GGT AAA GCC TAT GTG
CAT CCG TTT GAA CAA GGC AAA CAC ATT AAA GCC GAT AAA TTA GTA CAG TTC GAT
TCG GCA AAC GGT ATT ATT GAT GTG AGT AAT TCG GGT AAA GCG AAA ACT CAG CAT
```

-continued

```
ATC TTA TTC AGA ACG CCA TTA TTG ACG CCG GGA ACA GAG CAT CGT GAA CGC GTA
CAA ACA GGT AAA TAT GAA TAT ATT ACC AAG CTC AAT ATT AAC CGT GTA GAT AGC
TGG AAA ATT ACA GAT GGT GCA GCA AGT TCT ACC TTT GAT TTA ACT AAC GTT GTT
CAG CGT ATT GGT ATT GAA TTA GAC AAT GCT GGA AAT GTA ACT AAA ACC AAA GAA
ACA AAA ATT ATT GCC AAA CTT GGT GAA GGT GAT GAC AAC GTA TTT GTT GGT TCT
GGT ACG ACG GAA ATT GAT GGC GGT GAA GGT TAC GAC CGA GTT CAC TAT AGC CGT
GGA AAC TAT GGT GCT TTA ACT ATT GAT GCA ACC AAA GAG ACC GAG CAA GGT AGT
TAT ACC GTA AAT CGT TTC GTA GAA ACC GGT AAA GCA CTA CAC GAA GTG ACT TCA
ACC CAT ACC GCA TTA GTG GGC AAC CGT GAA GAA AAA ATA GAA TAT CGT CAT AGC
AAT AAC CAG CAC CAT GCC GGT TAT TAC ACC AAA GAT ACC TTG AAA GCT GTT GAA
GAA ATT ATC GGT ACA TCA CAT AAC GAT ATC TTT AAA GGT AGT AAG TTC AAT GAT
GCC TTT AAC GGT GGT GAT GGT GTC GAT ACT ATT GAC GGT AAC GAC GGC AAT GAC
CGC TTA TTT GGT GGT AAA GGC GAT GAT ATT CTC GAT GGT CGA AAT GGT GAT GAT
TTT ATC GAT GGC GGT AAA CCC AAC GAC CTA TTA CAC GGT GGC AAG GGC GAT GAT
ATT TTC GTT CAC CGT AAA GGC GAT GGT AAT GAT ATT ATT ACC GAT TCT GAG GGC
AAT GAT AAA TTA TCA TTC TCT CAT TCG AAC TTA AAA GAT TTA ACA TTT GAA AAA
GTT AAA CAT AAT CTT GTC ATC ACG AAT AGC AAA AAA GAG AAA GTG ACC ATT CAA
AAC TGG TTC CGA GAG GCT GAT TTT GCT AAA GAA GTG CCT AAT TAT AAA GCA ACT
AAA GAT GAG AAA ATC GAA GAA ATC ATC GGT CAA AAT GGC GAG CGG ATC ACC TCA
AAG CAA GTT GAT GAT CTT ATC GCA AAA GGT AAC GGC AAA ATT ACC AAA GAT GAG
CTA TCA AAA GTT GTT GAT AAC TAT GAA TTG CTC AAA CAT AGC AAA AAT GTG ACA
AAC AGC TTA GAT AAG TTA ATC TCA TCT GTA AGT GCA TTT ACC TCG TCT AAT GAT
TCG AGA AAT GTA TTA GTG GCT CCA ACT TCA ATG TTG GAT CAA AGT TTA TCT TCT
CTT CAA TTT GCT AGA GCA GCT TAA.
```

5. The substantially pure DNA sequence as claimed in claim 1, wherein said DNA sequence comprises the following DNA sequence, wherein T represents a thymine nucleotide, G represents a quanine nucleotide, A represents an adenine nucleotide and C represents a cytosine nucleotide:

```
                                                                ATG AAT CAA
TCT TAT TTT AAC TTA CTA GGA AAC ATT ACT TGG CTA TGG ATG AAC TCC TCC CTC
CAC AAA GAA TGG AGC TGT GAA CTA CTA GCA CGC AAT GTG ATT CCT CCA ATT GAA
AAT GAA CAA TAT ATG CTA CTT ATA GAT AAC GGT ATT CCG ATC GCT TAT TGT AGT
TCG GCA GAT TTA AAC CTT GAG ACT GAG GTG AAA TAT ATT AAG GAT ATT AAT TCG
TTA ACA CCA GAA GAA TCG CAG TCT GGT GAC AGA CGC TGG ATT ATT GAT TGG GTA
GCA CCA TTC GGA CAT TCT CAA TTA CTT TAT AAA AAA ATG TGT CAG AAA TAC CCT
GAT ATG ATC GTC AGA TCT ATA CGC TTT TAT CCA AAG CAG AAA GAA TTA GGC AAA
ATT GCC TAC TTT AAA GGA GGT AAA TTA GAT AAA AAA ACA GCA AAA AAA CGT TTT
GAT ACA TAT CAA GAA GAG CTG GCA ACA GCA CTT AAA AAT GAA TTT AAT TTT ATT
AAA AAA TAG AAGGAG ACATCCCTT ATG GGA ACT AGA CTT ACA ACC CTA TCA AAT
GGG CTA AAA AAC ACT TTA ACG GCA ACC AAA AGT GCC TTA CAT AAA GCC GGT CAA
TCA TTA ACC CAA GCC GGC AGT TCT TTA AAA ACT GGG GCA AAA AAA ATT ATC CTC
TAT ATT CCC CAA AAT TAC CAA TAT GAT ACT GAA CAA GGT AAT GGT TTA CAG GAT
```

-continued

```
TTA GTC AAA GCG GCC GAA GAG TTG GGC ATT GAG GTA CAA AGA GAA GAA CGC AAT
AAT ATT GCA ACA GCT CAA ACC AGT TTA GGC ACG ATT CAA ACC GCT ATT GGC TTA
ACT GAG CGT GGC ATT GTG TTA TCC GCT CCA CAA ATT GAT AAA TTG CTA CAG AAA
ACT AAA GCA GGC CAA GCA TTA GGT TCT GCC GAA AGC ATT GTA CAA AAT GCA AAT
AAA GCC AAA ACT GTA TTA TCT GGC ATT CAA TCT ATT TTA GGC TCA GTA TTG GCT
GCA ATG GAT TTA GAT GAG GCC TTA CAG AAT AAC AGC AAC CAA CAT GCT CTT GCT
AAA GCT GGC TTG GAG CTA ACA AAT TCA TTA ATT GAA AAT ATT GCT AAT TCA GTA
AAA ACA CTT GAC GAA TTT GGT GAG CAA ATT AGT CAA TTT GGT TCA AAA CTA CAA
AAT ATC AAA GGC TTA GGG ACT TTA GGA GAC AAA CTC AAA AAT ATC GGT GGA CTT
GAT AAA GCT GGC CTT GGT TTA GAT GTT ATC TCA GGG CTA TTA TCG GGC GCA ACA
GCT GCA CTT GTA CTT GCA GAT AAA AAT GCT TCA ACA GCT AAA AAA GTG GGT GCG
GGT TTT GAA TTG GCA AAC CAA GTT GTT GGT AAT ATT ACC AAA GCC GTT TCT TCT
TAC ATT TTA GCC CAA CGT GTT GCA GCA GGT TTA TCT TCA ACT GGG CCT GTG GCT
GCT TTA ATT GCT TCT ACT GTT TCT CTT GCG ATT AGC CCA TTA GCA TTT GGC GGT
ATT GCC GAT AAA TTT AAT CAT GCA AAA AGT TTA GAG AGT TAT GCC GAA CGC TTT
AAA AAA TTA GGC TAT GAC GGA GAT AAT TTA TTA GCA GAA TAT CAG CGG GGA ACA
GGG ACT ATT GAT GCA TCG GTT ACT GCA ATT AAT ACC GCA TTG GCC GCT ATT GCT
GGT GGT GTG TCT GCT GCT GCA GCC GGC TCG GTT ATT GCT TCA CCG ATT GCC TTA
TTA GTA TCT GGG ATT ACC GGT GTA ATT TCT ACG ATT CTG CAA TAT TCT AAA CAA
GCA ATG TTT GAG CAC GTT GCA AAT AAA ATT CAT AAC AAA ATT GTA GAA TGG GAA
AAA AAT AAT CAC GGT AAG AAC TAC TTT GAA AAT GGT TAC GAT GCC CGT TAT CTT
CCG AAT TTA CAA GAT AAT ATG AAA TTC TTA CTG AAC TTA AAC AAA GAG TTA CAG
GCA GAA CGT GTC ATC GCT ATT ACT CAG CAG CAA TGG GAT AAC AAC ATT GGT GAT
TTA GCT GGT ATT AGC CGT TTA GGT GAA AAA GTC CTT AGT GGT AAA GCC TAT GTG
CAT CCG TTT GAA GAA GGC AAA CAG ATT AAA GCC GAT AAA TTA GTA CAG TTG GAT
TCG GCA AAC GGT ATT ATT GAT GTC ACT AAT TCG CGT AAA GCG AAA ACT CAG CAT
ATC TTA TTC AGA ACG CCA TTA TTG ACG CCG GGA ACA GAG CAT CGT GAT GGC GTA
CAA ACA GGT AAA TAT GAA TAT ATT ACC AAG CTC AAT ATT AAC CGT GTA GAT AGC
TGG AAA ATT ACA GAT GGT GCA GCA AGT TCT ACC TTT GAT TTA ACT AAC GTT GTT
CAG CGT ATT GGT ATT GAA TTA GAC AAT GCT GGA AAT GTA ACT AAA ACC AAA GAA
ACA AAA ATT ATT GCC AAA CTT GGT GAA GGT GAT GAC AAC GTA TTT GTT GGT TCT
GGT ACG ACG GAA ATT GAT GGC GGT GAA GGT TAC GAC CGA GTT CAC TAT AGC CGT
GGA AAC TAT GGT GCT TTA ACT ATT GAT GCA ACC AAA GAG ACC GAG CAA GGT AGT
TAT ACC GTA AAT CGT TTC GTA GAA ACC GGT AAA GCA CTA CAC GAA GTC ACT TCA
ACC CAT ACC GCA TTA GTG GGC AAC CGT GAA GAA AAA ATA GAA TAT CGT CAT AGC
AAT AAC CAG CAC CAT GCC GGT TAT TAC ACC AAA GAT ACC TTG AAA GCT GTT GAA
GAA ATT ATC GGT ACA TCA CAT AAC GAT ATC TTT AAA GGT AGT AAG TTC AAT GAT
GCC TTT AAC GGT GGT GAT GGT GTC GAT ACT ATT GAC GGT AAC GAC CGC AAT GAC
CGC TTA TTT GGT GGT AAA GGC GAT GAT ATT CTC GAT GGT GGA AAT GGT GAT GAT
TTT ATC GAT GGC GGT AAA GGC AAC GAC CTA TTA CAC GGT GGC AAC GGC GAT GAT
ATT TTC GTT CAC CGT AAA GGC GAT GGT AAT GAT ATT ATT ACC GAT TCT GAC GGC
AAT GAT AAA TTA TCA TTC TCT GAT TCG AAC TTA AAA GAT TTA ACA TTT GAA AAA
```

-continued

```
GTT AAA CAT AAT CTT GTC ATC ACG AAT AGC AAA AAA GAG AAA GTG ACC ATT CAA
AAC TGG TTC CGA GAG GCT GAT TTT GCT AAA GAA GTG CCT AAT TAT AAA GCA ACT
AAA GAT GAG AAA ATC GAA GAA ATC ATC GGT CAA AAT GGC GAG CGG ATC ACC TCA
AAG CAA GTT GAT GAT CTT ATC GCA AAA GGT AAC GGC AAA ATT ACC CAA GAT GAG
CTA TCA AAA GTT GTT GAT AAC TAT GAA TTG CTC AAA CAT AGC AAA AAT GTG ACA
AAC AGC TTA GAT AAG TTA ATC TCA TCT GTA AGT GCA TTT ACC TCG TCT AAT GAT
TCG AGA AAT GTA TTA GTG GCT CCA ACT TCA ATG TTG GAT CAA AGT TTA TCT TCT
CTT CAA TTT GCT AGA GCA GCT TAA.
```

6. The substantially pure DNA sequence as claimed in claim 1, wherein said DNA sequence polymer encodes for leukotoxin protein having the following amino acid sequence:

```
                    Met Gly Thr Arg Leu Thr Thr Leu Ser Asn
Gly Leu Lys Asn Thr Leu Thr Ala Thr Lys Ser Gly Leu His Lys Ala Gly Gln
Ser Leu Thr Gln Ala Gly Ser Ser Leu Lys Thr Gly Ala Lys Lys Ile Ile Leu
Tyr Ile Pro Glu Asn Tyr Gln Tyr Asp Thr Glu Gln Gly Asn Gly Leu Gln Asp
Leu Val Lys Ala Ala Glu Glu Leu Gly Ile Glu Val Gln Arg Glu Glu Arg Asn
Asn Ile Ala Thr Ala Gln Thr Ser Leu Gly Thr Ile Gln Thr Ala Ile Gly Leu
Thr Glu Arg Gly Ile Val Leu Ser Ala Pro Gln Ile Asp Lys Leu Leu Gln Lys
Thr Lys Ala Gly Gln Ala Leu Gly Ser Ala Glu Ser Ile Val Gln Asn Ala Asn
Lys Ala Lys Thr Val Leu Ser Gly Ile Gln Ser Ile Leu Gly Ser Val Leu Ala
Gly Met Asp Leu Asp Glu Ala Leu Gln Asn Asn Ser Asn Gln His Ala Leu Ala
Lys Ala Gly Leu Glu Leu Thr Asn Ser Leu Ile Glu Asn Ile Ala Asn Ser Val
Lys Thr Leu Asp Glu Phe Gly Glu Gln Ile Ser Gln Phe Gly Ser Lys Leu Gln
Asn Ile Lys Gly Leu Gly Thr Leu Gly Asp Lys Leu Lys Asn Ile Gly Gly Leu
Asp Lys Ala Gly Leu Gly Leu Asp Val Ile Ser Gly Leu Leu Ser Gly Ala Thr
Ala Ala Leu Val Leu Ala Asp Lys Asn Ala Ser Thr Ala Lys Lys Val Gly Ala
Gly Phe Glu Leu Ala Asn Gln Val Val Gly Asn Ile Thr Lys Ala Val Ser Ser
Tyr Ile Leu Ala Gln Arg Val Ala Ala Gly Leu Ser Ser Thr Gly Pro Val Ala
Ala Leu Ile Ala Ser Thr Val Ser Leu Ala Ile Ser Pro Leu Ala Phe Ala Gly
Ile Ala Asp Lys Phe Asn His Ala Lys Ser Leu Glu Ser Tyr Ala Glu Arg Phe
Lys Lys Leu Gly Tyr Asp Gly Asp Asn Leu Leu Ala Glu Tyr Gln Arg Gly Thr
Gly Thr Ile Asp Ala Ser Val Thr Ala Ile Asn Thr Ala Leu Ala Ala Ile Ala
Gly Gly Val Ser Ala Ala Ala Ala Gly Ser Val Ile Ala Ser Pro Ile Ala Leu
Leu Val Ser Gly Ile Thr Gly Val Ile Ser Thr Ile Leu Gln Tyr Ser Lys Gln
Ala Met Phe Glu His Val Ala Asn Lys Ile His Asn Lys Ile Val Glu Trp Glu
Lys Asn Asn His Gly Lys Asn Tyr Phe Glu Asn Gly Tyr Asp Ala Arg Tyr Leu
Ala Asn Leu Gln Asp Asn Met Lys Phe Leu Leu Asn Leu Asn Lys Glu Leu Glu
Ala Glu Arg Val Ile Ala Ile Thr Gln Gln Gln Trp Asp Asn Asn Ile Gly Asp
Leu Ala Gly Ile Ser Arg Leu Gly Glu Lys Val Leu Ser Gly Lys Ala Tyr Val
Asp Ala Phe Glu Glu Gly Lys His Ile Lys Ala Asp Lys Leu Val Gln Leu Asp
Ser Ala Asn Gly Ile Ile Asp Val Ser Asn Ser Gly Lys Ala Lys Thr Gln His
```

-continued

Ile Leu Phe Arg Thr Pro Leu Leu Thr Pro Gly Thr Glu His Arg Glu Arg Val
Gln Thr Gly Lys Tyr Glu Tyr Ile Thr Lys Leu Asn Ile Asn Arg Val Asp Ser
Trp Lys Ile Thr Asp Gly Ala Ala Ser Ser Thr Phe Asp Leu Thr Asn Val Val
Gln Arg Ile Gly ILe Glu Leu Asp Asn Ala Gly Asn Val Thr Lys Thr Lys Glu
Thr Lys Ile Ile Ala Lys Leu Gly Glu Gly Asp Asp Asn Val Phe Val Gly Ser
Gly Thr Thr Glu Ile Asp Gly Gly Glu Gly Tyr Asp Arg Val His Tyr Ser Arg
Gly Asn Tyr Gly Ala Leu Thr Ile Asp Ala Thr Lys Glu Thr Glu Gln Gly Ser
Tyr Thr Val Asn Arg Phe Val Glu Thr Gly Lys Ala Leu His Glu Val Thr Ser
Thr His Thr Ala Leu Val Gly Asn Arg Glu Glu Lys Ile Glu Tyr Arg His Ser
Asn Asn Gln His His Ala Gly Tyr Tyr Thr Lys Asp Thr Leu Lys Ala Val Glu
Glu Ile Ile Gly Thr Ser His Asn Asp Ile Phe Lys Gly Ser Lys Phe Asn Asp
Ala Phe Asn Gly Gly Asp Gly Val Asp Thr Ile Asp Gly Asn Asp Gly Asn Asp
Arg Leu Phe Gly Gly Lys Gly Asp Asp Ile Leu Asp Gly Gly Asn Gly Asp Asp
Phe Ile Asp Gly Gly Lys Gly Asn Asp Leu Leu His Gly Gly Lys Gly Asp Asp
Ile Phe Val His Arg Lys Gly Asp Gly Asn Asp Ile Ile Thr Asp Ser Asp Gly
Asn Asp Lys Leu Ser Phe Ser Asp Ser Asn Leu Lys Asp Leu Thr Phe Glu Lys
Val Lys His Asn Leu Val Ile Thr Asn Ser Lys Lys Glu Lys Val Thr Ile Gln
Asn Trp Phe Arg Glu Ala Asp Phe Ala Lys Glu Val Pro Asn Tyr Lys Ala Thr
Lys Asp Glu Lys Ile Glu Glu Ile Ile Gly Gln Asn Gly Glu Arg Ile Thr Ser
Lys Gln Val Asp Asp Leu Ile Ala Lys Gly Asn Gly Lys Ile Thr Gln Asp Glu
Leu Ser Lys Val Val Asp Asn Tyr Glu Leu Leu Lys His Ser Lys Asn Val Thr
Asn Ser Leu Asp Lys Leu Ile Ser Ser Val Ser Ala Phe Thr Ser Ser Asn Asp
Ser Arg Asn Val Leu Val Ala Pro Thr Ser Met Leu Asp Gln Ser Leu Ser Ser
Leu Gln Phe Ala Arg Ala Ala.

7. The substantially pure DNA sequence as claimed in claim 1, wherein said DNA sequence encodes for leukotoxin protein having the following amino acid sequence:

Met Asn Gln
Ser Tyr Phe Asn Leu Leu Gly Asn Ile Thr Trp Leu trp Met Asn Ser Ser Leu
His Lys Glu Trp Ser Cys Glu Leu Leu Ala Arg Asn Val Ile Pro Ala Ile Glu
Asn Glu Gln Tyr Met Leu Leu Ile Asp Asn Gly Ile Pro Ile Ala Tyr Cys Ser
Trp Ala Asp Leu Asn Leu Glu Thr Glu Val Lys Tyr Ile Lys Asp Ile Asn Ser
Leu Thr Pro Glu Glu Trp Gln Ser Gly Asp Arg Arg Trp Ile Ile Asp Trp Val
Ala Pro Phe Gly His Ser Gln Leu Leu Tyr Lys Lys Met Cyc Gln Lys Tyr Pro
Asp Met Ile Val Arg Ser Ile Arg Phe Tyr Pro Lys Gln Lys Glu Leu Gly Lys
Ile Ala Tyr Phe Lys Gly Gly Lys Leu Asp Lys Lys Thr Ala Lys Lys Arg Phe
Asp Thr Tyr Gln Glu Glu Leu Ala Thr Ala Leu Lys Asn Glu Phe Asn Phe Ile
Lys Lys Met Gly Thr Arg Leu Thr Thr Leu Ser Asn
Gly Leu Lys Asn Thr Leu Thr Ala Thr Lys Ser Gly leu His Lys Ala Gly Gln
Ser Leu Thr Gln Ala Gly Ser Ser Les Lys Thr Gly Ala Lys Lys Ile Ile Leu
Tyr Ile Pro Gln Asn Tyr Gln Tyr Asp Thr Glu Gln Gly Asn Gly Leu Gln Asp Leu Val Lys Ala Ala Glu Glu Leu Gly Ile Glu Val Gln Arg Glu Glu Arg Asn

Asn Ile Ala Thr Ala Gln Thr Ser Leu Gly Thr Ile Gln Thr Ala Ile Gly Leu

Thr Glu Arg Gly Ile Val Leu Ser Ala Pro Gln Ile Asp Lys Leu Leu Gln Lys

Thr Lys Ala Gly Gln Ala Leu Gly Ser Ala Glu Ser Ile Val Gln Asn Ala Asn

Lys Ala Lys Thr Val Leu Ser Gly Ile Gln Ser Ile Leu Gly Ser Val Leu Ala

Gly Met Asp Leu Asp Glu Ala Leu Gln Asn Asn Ser Asn Gln His Ala Leu Ala

Lys Ala Gly Leu Glu Leu Thr Asn Ser Leu Ile Glu Asn Ile Ala Asn Ser Val

Lys Thr Leu Asp Glu Phe Glu Glu Gln Ile Ser Gln Phe Gly Ser Lys Leu Gln

Asn Ile Lys Gly Leu Gly Thr Leu Gly Asp Lys Leu Lys Asn Ile Gly Gly Leu

Asp Lys Ala Gly Leu Gly Leu Asp Val Ile Ser Gly Leu Leu Ser Gly Ala Thr

Ala Ala Leu Val Leu Ala Asp Lys Asn Ala Ser Thr Ala Lys Lys Val Gly Ala

Gly Phe Glu Leu Ala Asn Gln Val Val Gly Asn Ile Thr Lys Ala Val Ser Ser

Tyr Ile Leu Ala Gln Arg Val Ala Ala Gly Leu Ser Ser Thr Gly Pro Val Ala

Ala Leu Ile Ala Ser Thr Val Ser Leu Ala Ile Ser Pro Leu Ala Phe Ala Gly

Ile Ala Asp Lys Phe Asn His Ala Lys Ser Leu Glu Ser Tyr Ala Glu Arg Phe

Lys Lys Leu Gly Tyr Asp Gly Asp Asn Leu Leu Ala Glu Tyr Gln Arg Gly Thr

Gly Thr Ile Asp Ala Ser Val Thr Ala Ile Asn Thr Ala Leu Ala Ala Ile Ala

Gly Gly Val Ser Ala Ala Ala Ala Gly Ser Val Ile Ala Ser Pro Ile Ala Leu

Leu Val Ser Gly Ile Thr Gly Val Ile Ser Thr Ile Leu Gln tyr Ser Lys Gln

Ala Met Phe Glu His Val Ala Asn Lys Ile His Asn Lys Ile Val Glu Trp Glu

Lys Asn Asn His Gly Lys Asn Tyr Phs Glu Asn Gly Tyr Asp Ala Arg Tyr Leu

Ala Asn Leu Gln Asp Asu Met Lys Phe Leu Leu Asn Leu Asn Lys Glu Leu Gln

Ala Glu Arg Val Ile Ala Ile Thr Gln Gln Gln Trp Asp Asn Asn Ile Gly Asp

Leu Ala Gly Ile Ser Arg Leu Gly Glu Lys Val Leu Ser Gly Lys Ala Tyr Val

Asp Ala Phe Glu Glu Gly Lys His Ile Lys Ala Asp Lys Leu Val Gln Leu Asp

Ser Ala Asn Gly Ile Ile Asp Val Ser Asn Ser Gly Lys Ala Lys Thr Gln His

Ile Leu Phe Arg Thr Pro Leu Leu Thr Pro Gly Thr Glu His Arg Glu Arg Val

Gln Thr Gly Lys Tyr Glu Tyr Ile Thr Lys Leu Asn Ile Asn Arg Val Asp Ser

Trp Lys Ile Thr Asp Gly Ala Ala Ser Ser Thr Phe Asp Leu Thr Asn Val Val

Gln Arg Ile Gly Ile Glu Leu Asp Asn Ala Gly Asn Val Thr Lys Thr Lys Glu

Thr Lys Ile Ile Ala Lys Leu Glu Glu Gly Asp Asp Asn Val Phe Val Gly Ser

Gly Thr Thr Glu Ile Asp Gly Gly Glu Gly Tyr Asp Arg Val His Tyr Ser Arg

Tyr Thr Val Asn Arg Phe Val Glu Thr Gly Lys Ala Leu His Glu Val Thr Ser

Thr His Thr Ala Leu Val Gly Asn Arg Glu Glu Lys Ile Glu Tyr Arg His Ser

Asn Asn Glu His His Ala Gly Tyr Tyr Thr Lys Asp Thr Leu Lys Ala Val Glu

Glu Ile Ile Gly Thr Ser His Asn Asp Ile Phe Lys Gly Ser Lys Phe Asn Asn

Ala Phe Asn Gly Gly Asp Gly Val Asp Thr Ile Asp Gly Asn Asp Gly Asn Asp

Arg Leu Phe Gly Gly Lys Gly Asp Asp Ile Leu Asp Gly gly Asn Gly Asp Asp

Phe Ile Asp Gly Gly Lys Gly Asn Asp Leu Leu His Gly Gly Lys Gly Asp Asp

Ile Phe Val His Arg Lys Gly Asp Gly Asn Asp Ile Ile Thr Asp Ser Asp Gly

Asn Asp Lys Leu Ser Phe Ser Asp Ser Asn Leu Lys Asp Leu Thr Phe Glu Lys

-continued

Val Lys His Asn Leu Val Ile Thr Asn Ser Lys Lys Glu Lys Val Thr Ile Gln

Asn Trp Phe Arg Glu Ala Asp Phe Ala Lys Glu Val Pro Asn Tyr Lys Ala Thr

Lys Asp Glu Lys Ile Glu Glu Ile Ile Gly Gln Asn Gly Glu Arg Ile Thr Ser

Leu Ser Lys Val Val Asp Asn Tyr Glu Leu Leu Lys His Ser Lys Asn Val Thr

Asn Ser Leu Asp Lys Leu Ile Ser Ser Val Ser Ala Phe Thr Ser Ser Asn Asp

Ser Arg Asn Val Leu Val Ala Pro Thr Ser Met Leu Asp Gln Ser Leu Ser Ser

Leu Gln Phe Ala Arg Ala Ala.

8. The substantially pure DNA sequence as claimed in claim 4, wherein the entire DNA sequence or portion thereof is used as a DNA probe.

9. The substantially pure DNA sequence as claimed in claim 1, wherein said DNA sequence is derived from *Pasteurella haemolytica* A1.

10. The substantially pure DNA sequence as claimed in claim 4, wherein said DNA sequence is derived from *Pasteurella haemolytica* A1.

11. The substantially pure DNA sequence as claimed in claim 5, wherein said DNA sequence is derived from *Pasteurella haemolytica* A1.

12. A recombinant plasmid vector containing said DNA polymer of claim 1.

13. The recombinant plasmid vector as claimed in claim 12, wherein said recombinant plasmid is pLKT5.

14. A phage vector containing said DNA sequence of claim 1.

15. A microorganism transformed with the recombinant plasmid vector of claim 12.

16. The microorganism as claimed in claim 15, wherein said microorganism is *Escherichia coli*.

17. The microorganism as claimed in claim 16, wherein said microorganism is transformed with recombinant plasmid having the identifying characteristics of ATCC No. 68025.

18. A process for producing a foreign proteinous leukotoxin comprising transforming a microorganism with said DNA sequence of claim 1, culturing the resulting transformed microorganism, obtaining the resulting leukotoxin produced from said cultured transformed microorganism.

19. The process as claimed in claim 18, wherein said DNA polymer comprises the DNA sequence claimed in claim 4.

20. The process as claimed in claim 18, wherein said leukotoxin has the amino acid sequence claimed in claim 6.

* * * * *